(12) United States Patent
Ying et al.

(10) Patent No.: US 11,965,805 B2
(45) Date of Patent: Apr. 23, 2024

(54) SAMPLING DEVICE AND METHOD FOR EVALUATING ECOLOGICAL RISK OF SOIL IN HIGH GEOLOGICAL BACKGROUND AREA

(71) Applicants: Nanjing Institute of Environmental Sciences, MEE, Nanjing (CN); Anhui Provincial Academy of Eco-Environmental Science Research, Hefei (CN)

(72) Inventors: Rongrong Ying, Nanjing (CN); Wenbing Ji, Nanjing (CN); Caiyi Zhao, Nanjing (CN); Bing Xia, Hefei (CN); Yuanyuan Lu, Nanjing (CN); Xiaoyu Zhang, Nanjing (CN); Zhewei Hu, Nanjing (CN); Yanhong Feng, Nanjing (CN); Qi Li, Nanjing (CN); Aijing Yin, Nanjing (CN); Hongfeng Chen, Hefei (CN)

(73) Assignees: Nanjing Institute of Environmental Sciences, MEE, Nanjing (CN); Anhui Provincial Academy of Eco-Environmental Science Research, Hefei (CN)

( * ) Notice: Subject to any disclaimer, the term of this patent is extended or adjusted under 35 U.S.C. 154(b) by 0 days.

(21) Appl. No.: 18/334,352

(22) Filed: Jun. 13, 2023

(65) Prior Publication Data
US 2024/0102891 A1 Mar. 28, 2024

(30) Foreign Application Priority Data
Sep. 22, 2022 (CN) .......................... 202211157386.8

(51) Int. Cl.
*G01N 1/08* (2006.01)
*G01N 33/24* (2006.01)

(52) U.S. Cl.
CPC ............... *G01N 1/08* (2013.01); *G01N 33/24* (2013.01)

(58) Field of Classification Search
CPC ................................. G01N 1/08; G01N 33/24
(Continued)

(56) References Cited

FOREIGN PATENT DOCUMENTS

| CN | 107478463 A | * | 12/2017 | ............... G01N 1/08 |
| CN | 108760381 A | * | 11/2018 | ............... G01N 1/08 |

(Continued)

OTHER PUBLICATIONS

Patent Search Report, prepared by Beijing Zhanqiao Patent Agency, dated Sep. 22, 2022.
(Continued)

*Primary Examiner* — Daniel S Larkin
*Assistant Examiner* — Nashmiya S Fayyaz
(74) *Attorney, Agent, or Firm* — Zhu Lehnhoff LLP

(57) ABSTRACT

A sampling device and method for evaluating ecological risk of soil in a high geological background area comprises an impact sampling mechanism, a soil layer stripping mechanism and an auxiliary support frame. The impact sampling mechanism comprises a sampling hopper with a downward opening. A connecting sliding rod is fixedly arranged on the top of the sampling hopper. An upper end of the connecting sliding rod is connected with an impact rod. The impact rod is internally provided with an impact hammer capable of reciprocating along an axis of the impact rod. The soil layer stripping mechanism comprises a stripping sliding cylinder in sliding fit with the connecting sliding rod, and a support disc. A plurality of stripping plates are connected to a lower side edge of the support disc in a sliding fit mode.

20 Claims, 11 Drawing Sheets

(58) Field of Classification Search
USPC .................................................. 73/864.45
See application file for complete search history.

(56) References Cited

FOREIGN PATENT DOCUMENTS

| | | | |
|---|---|---|---|
| CN | 215296732 U | | 12/2021 |
| CN | 114216722 A | * | 3/2022 |
| CN | 215931348 U | | 3/2022 |
| CN | 216524913 U | | 5/2022 |
| CN | 216955232 U | | 7/2022 |

OTHER PUBLICATIONS

Notice of Grant of Invention Patent, issued in Chinese priority application 202211157386.8, by CNIPA, dated Apr. 22, 2023.
Search Report, issued in Chinese priority application 2022111573868, by CNIPA, dated Sep. 22, 2022.

* cited by examiner

SAMPLING DEVICE AND METHOD FOR EVALUATING ECOLOGICAL RISK OF SOIL IN HIGH GEOLOGICAL BACKGROUND AREA

REFERENCE TO RELATED APPLICATIONS

The present application claims the priority of Chinese patent application No. 202211157386.8, filed on 2022 Sep. 22, the entire disclose of which is incorporated herein by reference.

TECHNICAL FIELD OF THE INVENTION

The present disclosure relates to the technical field of soil sample collection, in particular to a sampling device and method for evaluating ecological risk of soil in a high geological background area.

BACKGROUND OF THE INVENTION

In a high geological background, the enrichment of chemical elements such as heavy metals in soil is independent of human influence, but is related to soil forming rock and weathering and soil forming processes of the soil forming rock. The spatial distribution is associated with specific geological bodies. The contents of heavy metals such as As, Cd, Pb and Hg in soil are significantly higher than those in regional soil background values (such as karst areas) or areas where the biological activity of heavy metals in soil is significantly increased (such as black rock series distribution areas). The high geological background causes heavy metals in soil to exceed the standard, resulting in ecological problems and environmental problems to which more and more researchers pay attention.

In the case of collecting a large number of soil samples for research, the efficiency of manual excavation by workers is very low, and the physical fatigue of the body is unbearable, so a device is needed to assist workers to collect a large number of complete and effective soil samples efficiently, and the device needs to be portable.

SUMMARY OF THE INVENTION

The present disclosure aims to provide a sampling device and method for evaluating ecological risk of soil in a high geological background area. A soil layer sample can be collected efficiently and completely.

In order to achieve the above purposes, the present disclosure provides the following technical scheme.

A sampling device for evaluating ecological risk of soil in a high geological background area includes an impact sampling mechanism, a soil layer stripping mechanism and an auxiliary support frame.

The impact sampling mechanism includes a sampling hopper with a downward opening. A connecting sliding rod is fixedly arranged on the top of the sampling hopper. An upper end of the connecting sliding rod is connected with an impact rod.

The impact rod is of a hollow structure. The impact rod is internally provided with an impact hammer capable of reciprocating along an axis of the impact rod. The impact hammer is motor-driven to reciprocate along the axis of the impact rod through a crank-link mechanism.

The soil layer stripping mechanism includes a stripping sliding cylinder in sliding fit with the connecting sliding rod. A support disc is fixedly arranged on the stripping sliding cylinder. A plurality of stripping plates are connected to a lower side edge of the support disc in a sliding fit mode. The stripping plates are motor-driven and can move along a radial direction of the support disc.

The stripping plates are combined into an annular structure surrounding the outer side of the sampling hopper. Dimensions of the annular structure combined by the stripping plates along an axial direction of the sampling hopper need to be larger than axial dimensions of the sampling hopper.

The auxiliary support frame includes a stable support cylinder connected to the outer side of the stripping sliding cylinder in a sliding fit mode. A stable support plate is fixedly arranged on the stable support cylinder. A lower side of the stable support plate is connected with a plurality of telescopic stable legs.

Preferably, the impact hammer in the impact rod is driven by a linear motor to reciprocate along the axis of the impact rod.

A piston cylinder is fixedly arranged in the impact rod. The impact hammer is in sliding fit in the piston cylinder. A driving piston is arranged in the piston cylinder in a sliding fit mode above the impact hammer. A linear motor extending along an axial direction of the impact rod is fixedly arranged in the impact rod. An impact driving rod is connected between a rotor of the linear motor and the top of the driving piston. Both ends of the impact driving rod are connected in the form of spherical hinges.

Preferably, a plurality of radial sliding grooves extending along the radial direction and running from top to down are formed in the support disc. A stripping plate connecting rod is fixedly arranged on the top of the stripping plate. The stripping plate connecting rod extends upward through the radial sliding grooves. An upper end of the stripping plate connecting rod is connected with the stripping sliding cylinder in the form of a living hinge.

A reset spring is arranged between an inner side wall, away from the stripping sliding cylinder, of the radial sliding groove and one side, away from the stripping sliding cylinder, of the stripping plate connecting rod in a jacking fit mode. One side, close to the stripping sliding cylinder, of the stripping plate connecting rod is provided with a wedge block in a sliding fit mode.

The outer side of the stripping sliding cylinder is connected with a stripping plate control ring in a screw thread fit mode. A first gear ring is fixedly arranged on the stripping plate control ring. The outer side of the stripping sliding cylinder is connected with a first gear in a running fit mode. The first gear is connected with the first gear ring in a meshed mode. The first gear is motor-driven.

A lifting driving disc is fixedly at a lower end of the stripping plate control ring. A lifting constraint slot is formed in one side, close to the stripping sliding cylinder, of the wedge block. An edge of the lifting driving disc is constrained in the lifting constraint slot.

Preferably, A manual driving cylinder is fixedly arranged on the top of the first gear. An inner hexagonal hole is formed in the top of the manual driving cylinder.

That is to say, when the equipment is in a power shortage state, the first gear can be manually driven to rotate by using a handle with a hexagon screwdriver at one end.

Preferably, Upper and lower ends of the lifting constraint groove are provided with end face constraint rollers in a running fit mode. An inner side wall, close to the stripping sliding cylinder, of the radial sliding groove is connected with a lateral constraint roller in a running fit mode.

That is to say, the end face constraint roller and lateral constraint roller can greatly reduce the friction between parts, so that the parts are convenient to operate more stably.

Preferably, a plurality of sector ring accommodating grooves are formed in a lower side of the support disc. A plurality of telescopic through holes running from top to bottom are formed in the support plate and located at the sector ring accommodating grooves.

A telescopic control column is fixedly arranged on the top of the support disc and at the telescopic through holes. The telescopic control column is of a hollow structure. The telescopic control column is internally provided with a telescopic rod in a sliding fit mode. A rotating fit hole running from top to bottom is formed in the telescopic rod. The rotating fit hole is internally provided with a rotating rod in a running fit mode.

A low end of the rotating rod extends through the telescopic through holes. A cutting plate is fixedly arranged at a lower end of the rotating rod.

A first motor is fixedly arranged in the top of the telescopic control column. The first motor drives the telescopic rod to move along an axis of the telescopic control column through a screw lead mechanism. A second motor is fixedly arranged on the top of the telescopic rod. The second motor is used for driving the rotating rod to rotate in the rotating fit hole.

That is to say, the cutting plates can cut and separate the soil sample accommodated in the sampling hopper from the outside, and the cutting plates also play a role in supporting and protecting the soil sample in the sampling hopper, so that the complete and clear soil sample is obtained.

A driving fit plate is fixedly arranged on the telescopic rod. A threaded hole running from top to bottom is formed in the driving fit plate. A threaded rod is fixedly arranged on an output shaft of the first motor. The threaded rod is in threaded running fit in the threaded hole.

Preferably, an upper end of the stable leg is connected with the lower side of the stable support plate through a living hinge. The stable leg includes a leg fixing cylinder and a leg telescopic rod in sliding fit in the leg fixing cylinder. Sliding damping of the leg telescopic rod in the leg fixing cylinder is adjustable. A socket cone is fixedly arranged at a lower end of the leg telescopic rod.

That is to say, the stable legs play a role in supporting and stabilizing the whole device to prevent the sampling hopper from running off when drilling underground.

Preferably, the top of the stable support cylinder is provided with a first limit locking screw in a running fit mode. The top of the stripping sliding cylinder is provided with a second limit locking screw in a running fit mode.

A plurality of first locking grooves are formed in the outer side of the stripping sliding cylinder. A plurality of second locking grooves are formed in the outer side of the connecting sliding rod.

A screw cap of the first limit locking screw can be clamped in the first locking groove. A screw cap of the second limit locking screw can be clamped in the second locking groove.

A notch consistent with radian of an outer side wall of the stripping sliding cylinder is formed in the screw cap of the first limit locking screw. A notch consistent with radian of an outer side wall of the connecting sliding rod is formed in the screw cap of the second limit locking screw.

That is to say, the first limit locking screw and the second limit locking screw can be correspondingly clamped in the first locking groove and the second locking groove, so that the positions of the stable support cylinder and the stripping sliding cylinder are relatively fixed, and the positions of the stripping sliding cylinder and the connecting sliding rod are relatively fixed.

Preferably, the impact rod is matched with an impact connecting rod and an impact connecting cylinder. A lower end of the impact rod is provided with a threaded connecting pipe. Upper ends of the impact connecting rod and the impact connecting cylinder can be matched and fixedly connected with the threaded connecting pipe. A lower end of the impact connecting rod can be matched and fixedly connected with the top of the connecting sliding rod. An outer diameter of the impact connecting rod needs to be smaller than an inner diameter of the stripping sliding cylinder. The impact connecting cylinder is of a cylindrical structure with a downward opening. A lower end of the impact connecting cylinder can be matched and fixedly connected with the top of the stripping sliding cylinder. An inner diameter of the impact connecting cylinder needs to be larger than an outer diameter of the connecting sliding rod.

That is to say, the impact connecting rod and the impact connecting cylinder can be used for connecting the impact rod with the connecting sliding rod and the stripping sliding cylinder more quickly.

Preferably, a soil sampling method for a high geological background area by using the sampling device for evaluating ecological risk of soil in a high geological background area includes the following steps:

S1, firstly, leveling a surface of a position to be sampled, then placing the whole device at the position to be sampled, and inserting the socket cone at the lower end of the leg telescopic rod into the ground to stably support the whole device;

S2, connecting the impact rod with the top of the connecting sliding rod, and inserting the sampling hopper into the soil under the impact effect of a reciprocating motion of the impact hammer in the impact rod, so that a soil sample is accommodated in the sampling hopper;

S3, dismantling the impact rod from the top of the connecting sliding rod and then connecting the impact rod with the top of the stripping sliding cylinder, and impacting and inserting the stripping plates into the soil under the impact effect of the reciprocating motion of the impact hammer in the impact rod, so that the outer side of the sampling hopper is surrounded by the stripping plates;

S4, driving the first gear to rotate by a motor or manually, then driving the stripping plate control ring to rotate and driving the lifting drive disc to move downwards along an axis of the stripping plate control ring, further driving the wedge block to move by the lifting driving disc, and forcing the stripping plate to get away from the sampling hopper in the moving process by the wedge block;

S5, after a gap is formed between the stripping plates and the sampling hopper, enabling the telescopic rod together with the rotating rod and the cutting plate, to move downwards in the gap between the stripping plates and the sampling hopper under the driving of the first motor;

S6, when an upper surface of the cutting plate is flush with a lower end face of the sampling hopper, driving the rotating rod to rotate by the second motor and driving the cutting plate to cut and strip the soil sample in the sampling hopper from the outside; and S7, finally, separately detaching the sampling hopper together with the connecting sliding rod, connecting the impact rod with the top of the connecting sliding rod, and separating the soil sample in the sampling hopper by the impact effect of the impact rod and putting the soil sample into a sample container.

Compared with the prior art, the present disclosure has the beneficial effects that the sampling device is reasonable in structural design and convenient in operation and the whole device is compact and portable. The workload of workers can be effectively reduced under the condition that multiple times of sampling are needed. The soil sample can be drilled effectively and quickly by using the impact effect of the impact rod. The integrity of the soil sample can be ensured as much as possible during the soil sampling process, so that the soil layer structure is analyzed by the workers more accurately.

Reference signs: 10, impact sampling mechanism; 11, sampling hopper; 12, connecting sliding rod; 121, second locking groove; 13, impact rod; 131, impact hammer; 132, driving piston; 133, linear motor; 134, impact driving rod; 135, threaded connecting pipe; 136, impact connecting rod; 137, impact connecting cylinder; 20, soil layer stripping mechanism; 21, stripping sliding cylinder; 211, support disc; 212, radial sliding groove; 213, sector ring accommodating groove; 214, telescopic through hole; 215, second limit locking screw; 216, first locking groove; 22, stripping plate; 221, stripping plate connecting rod; 222, reset spring; 23, stripping plate control ring; 231, first gear ring; 232, first gear; 233, lifting driving disc; 234, manual driving cylinder; 24, wedge block; 241, lifting constraint slot; 242, end face constraint roller; 243, lateral constraint roller; 28, telescopic control column; 281, telescopic rod; 282, rotating fit hole; 283, rotating rod; 284, cutting plate; 285, first motor; 286, second motor; 287, driving fit plate; 288, threaded hole; 289, threaded rod; 30, auxiliary support frame; 31, stable support cylinder; 32, stable support plate; 33, stable leg; 331, leg fixing cylinder; 332, leg telescopic rod; and 333, socket cone.

DETAILED DESCRIPTION

The present disclosure is described in detail with reference to FIG. 1 to FIG. 10. For the convenience of description, the following directions are specified as follows: upper, lower, left, right, front and back directions mentioned below are consistent with those in a projection relationship of front views or structural schematic diagrams.

Embodiment I

Figure 1:
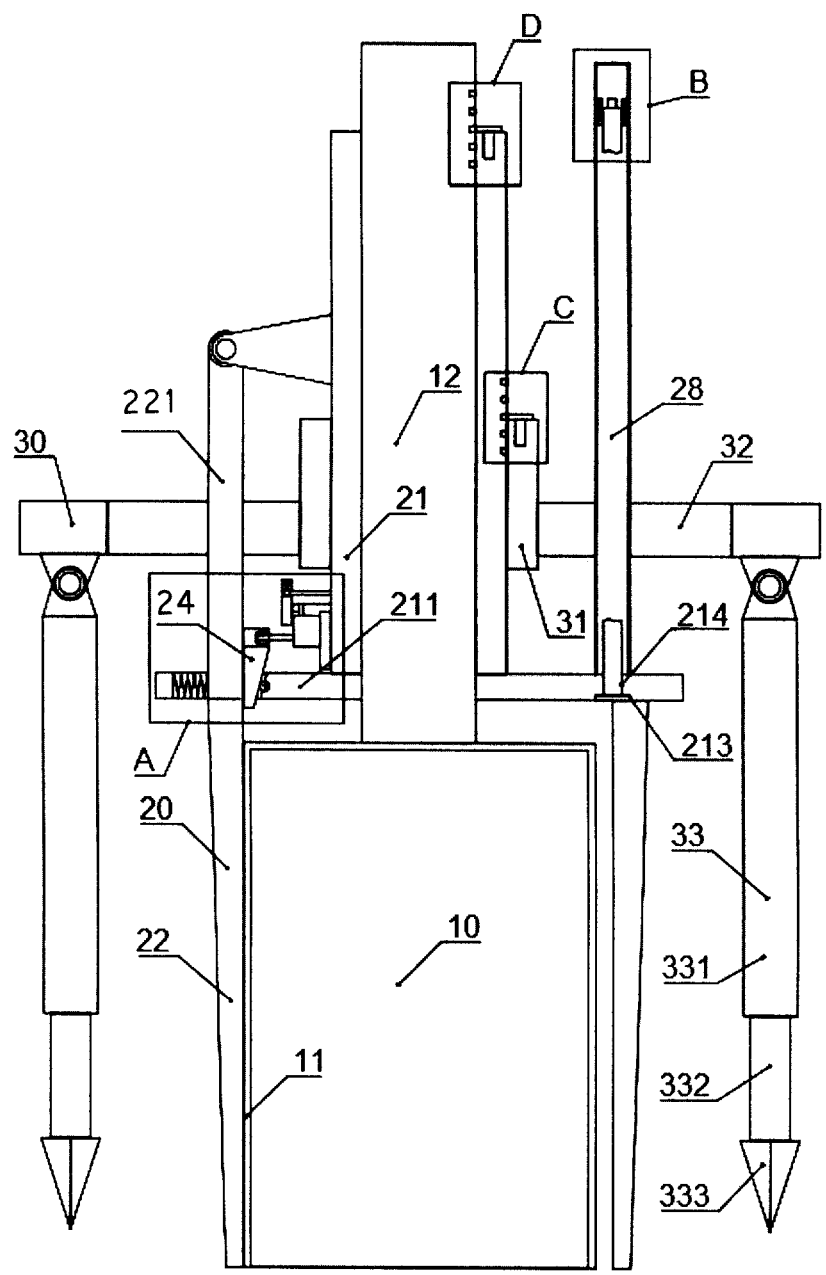
FIG. 1 is a front view of the present disclosure.
Figure 2:
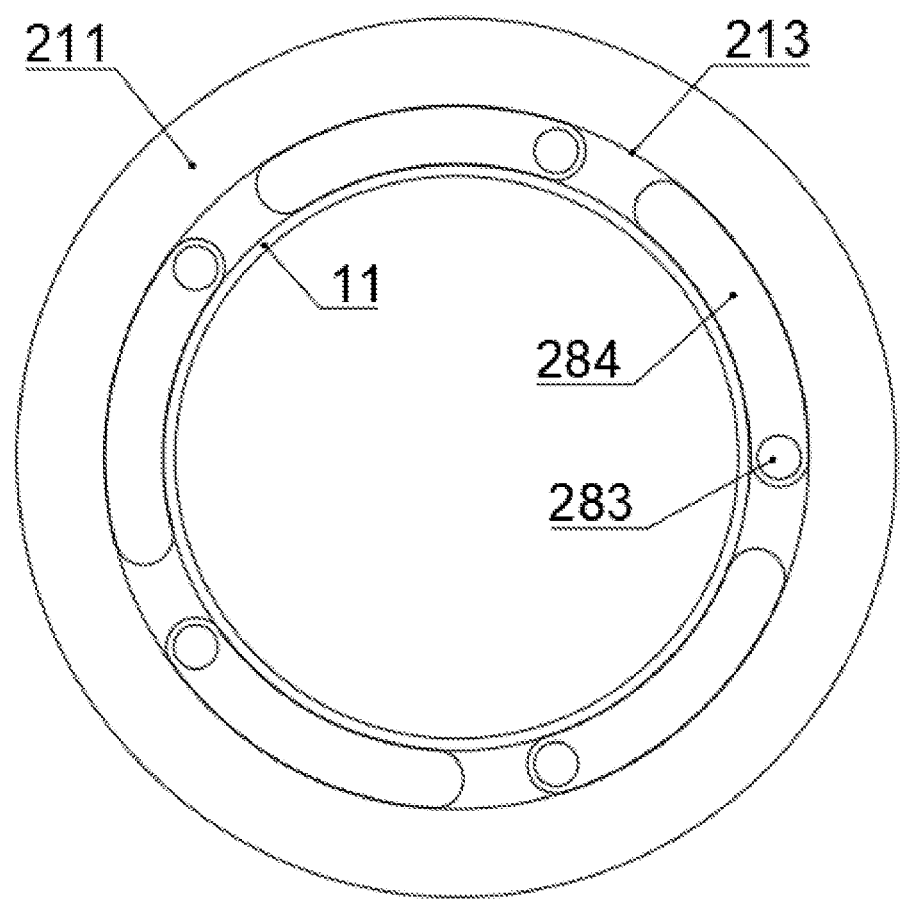
FIG. 2 is an upward view of FIG. 1.

The present disclosure provides a sampling device and method for evaluating ecological risk of soil in a high geological background area. As shown in FIG. 1, the sampling device includes an impact sampling mechanism 10, a soil layer stripping mechanism 20 and an auxiliary support frame 30.

As shown in FIG. 1, the impact sampling mechanism 10 includes a sampling hopper 11 with a downward opening. A connecting sliding rod 12 is fixedly arranged on the top of the sampling hopper 11. An upper end of the connecting sliding rod 12 is connected with an impact rod 13.

The impact rod 13 is of a hollow structure. The impact rod 13 is internally provided with an impact hammer 131 capable of reciprocating along an axis of the impact rod 13. The impact hammer 131 is motor-driven to reciprocate along the axis of the impact rod 13 through a crank-link mechanism.

As shown in FIG. 1, the soil layer stripping mechanism 20 includes a stripping sliding cylinder 21 in sliding fit with the connecting sliding rod 12. A support disc 211 is fixedly arranged on the stripping sliding cylinder 21. A plurality of stripping plates 22 are connected to a lower side edge of the support disc 211 in a sliding fit mode. The stripping plates 22 are motor-driven and can move along a radial direction of the support disc 211. The stripping plate 22 is of a tapered structure with a narrow bottom and a wide top.

The stripping plates 22 are combined into an annular structure surrounding the outer side of the sampling hopper 11, and dimensions of the annular structure combined by the stripping plates 22 along an axial direction of the sampling hopper 11 need to be larger than axial dimensions of the sampling hopper 11.

Figure 3:
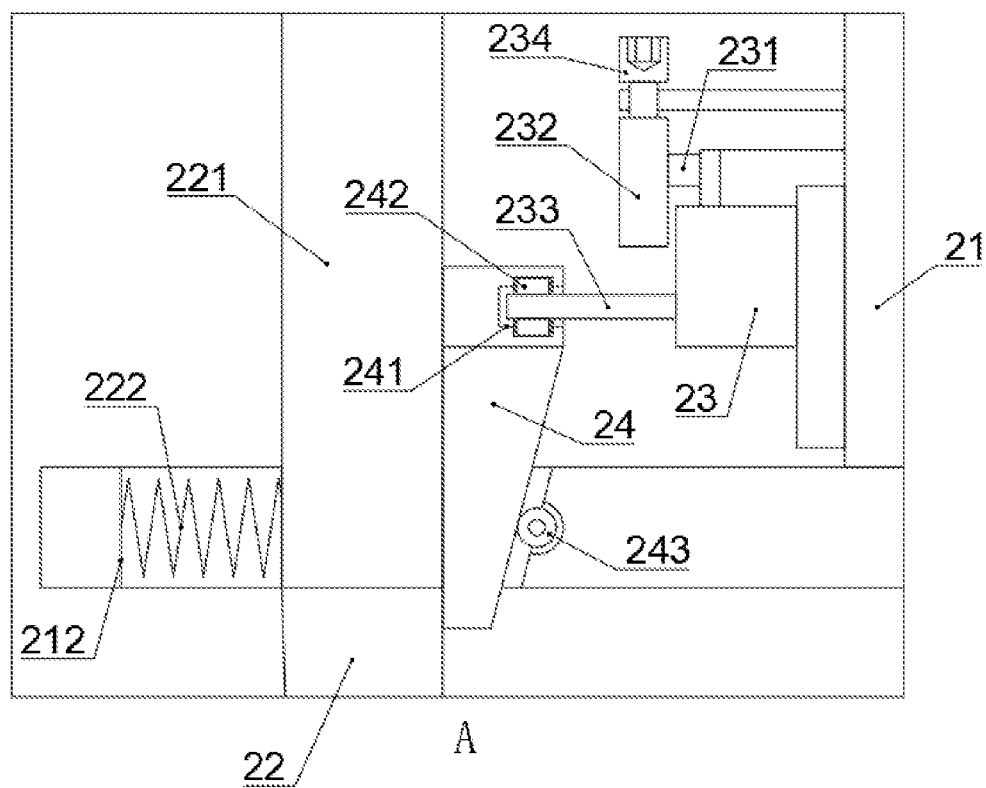
FIG. 3 is a partial view A of FIG. 1.

As shown in FIG. 3, a plurality of radial sliding grooves 212 extending along the radial direction and running from top to down are formed in the support disc 211. A stripping plate connecting rod 221 is fixedly arranged on the top of the stripping plate 22. The stripping plate connecting rod 221 extends upward through the radial sliding grooves 212. An upper end of the stripping plate connecting rod 221 is connected with the stripping sliding cylinder 21 in the form of a living hinge.

A reset spring 222 is arranged between an inner side wall, away from the stripping sliding cylinder 21, of the radial sliding groove 212 and one side, away from the stripping sliding cylinder 21, of the stripping plate connecting rod 221 in a jacking fit mode. One side, close to the stripping sliding cylinder 21, of the stripping plate connecting rod 221 is provided with a wedge block 24 in a sliding fit mode. The wedge block 24 is of a wedge structure with a narrow bottom and a wide top.

The outer side of the stripping sliding cylinder 21 is connected with a stripping plate control ring 23 in a screw thread fit mode. A first gear ring 231 is fixedly arranged on the stripping plate control ring 23. The outer side of the stripping sliding cylinder 21 is connected with a first gear 232 in a running fit mode. The first gear 232 is connected with the first gear ring 231 in a meshed mode. The first gear 232 is motor-driven.

A manual driving cylinder 234 is fixedly arranged on the top of the first gear 232. An inner hexagonal hole is formed in the top of the manual driving cylinder 234.

As shown in FIG. 3, a lifting driving disc 233 is fixedly at a lower end of the stripping plate control ring 23. A lifting constraint slot 241 is formed in one side, close to the stripping sliding cylinder 21, of the wedge block 24. An edge of the lifting driving disc 233 is constrained in the lifting constraint slot 241.

Upper and lower ends of the lifting constraint groove 241 are provided with end face constraint rollers 242 in a running fit mode. An inner side wall, close to the stripping sliding cylinder 21, of the radial sliding groove 212 is connected with a lateral constraint roller 243 in a running fit mode.

As shown in FIG. 1, a plurality of sector ring accommodating grooves 213 are formed in a lower side of the support disc 211. A plurality of telescopic through holes 214 running from top to bottom are formed in the support plate 211 and located at the sector ring accommodating grooves 213.

Figure 4:
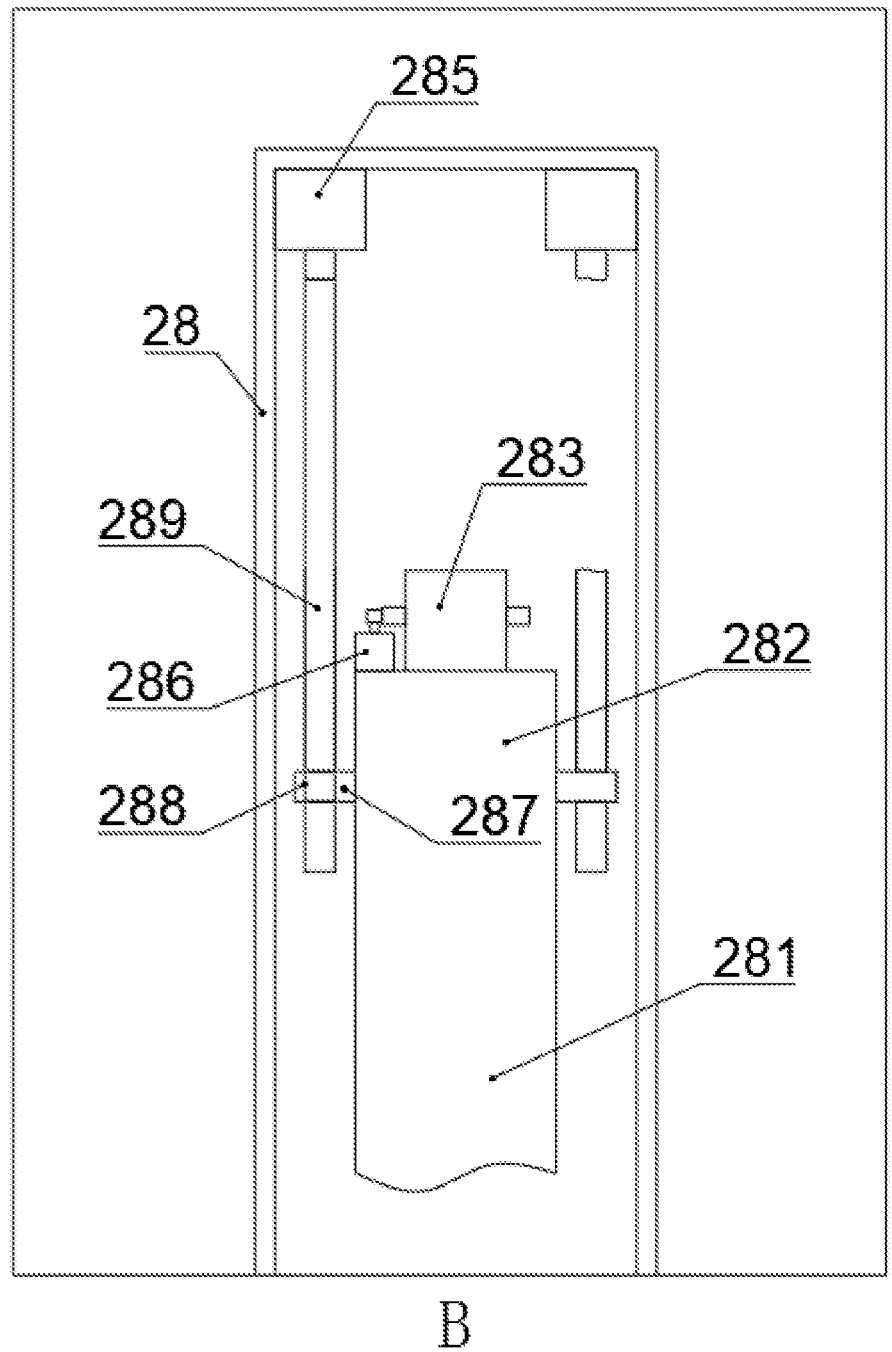
FIG. 4 is a partial view B of FIG. 1.

A telescopic control column 28 is fixedly arranged on the top of the support disc 211 and at the telescopic through holes 214. As shown in FIG. 4, the telescopic control column 28 is of a hollow structure. The telescopic control column 28 is internally provided with a telescopic rod 281 in a sliding fit mode. A rotating fit hole 282 running from top to bottom is formed in the telescopic rod 281. The rotating fit hole 282 is internally provided with a rotating rod 283 in a running fit mode.

A low end of the rotating rod 283 extends through the telescopic through holes 214. A cutting plate 284 is fixedly arranged at a lower end of the rotating rod 283.

As shown in FIG. 4, a first motor 285 is fixedly arranged in the top of the telescopic control column 28. The first motor 285 drives the telescopic rod 281 to move along an axis of the telescopic control column 28 through a screw lead mechanism. A second motor 286 is fixedly arranged on the top of the telescopic rod 281. The second motor 286 is used for driving the rotating rod 283 to rotate in the rotating fit hole 282.

A driving fit plate 287 is fixedly arranged on the telescopic rod 281. A threaded hole 288 running from top to bottom is formed in the driving fit plate 287. A threaded rod 289 is fixedly arranged on an output shaft of the first motor 285. The threaded rod 289 is in threaded running fit in the threaded hole 288.

Figure 9:
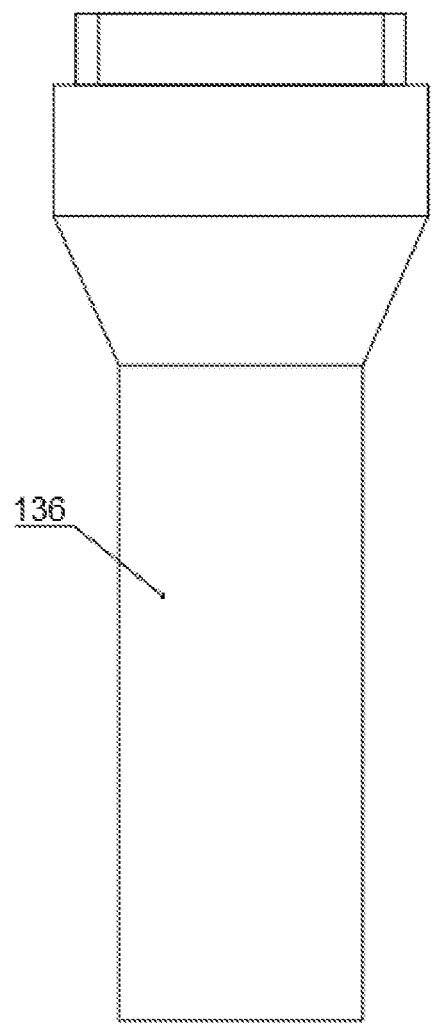
FIG. 9 is a structural schematic diagram of an impact connecting rod in the present disclosure.
Figure 10:
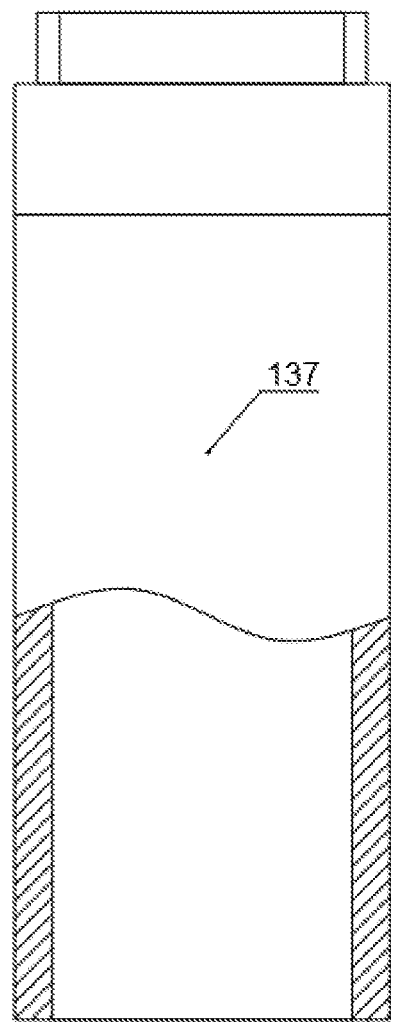
FIG. 10 is a structural schematic diagram of an impact connecting cylinder in the present disclosure.
Figure 11:
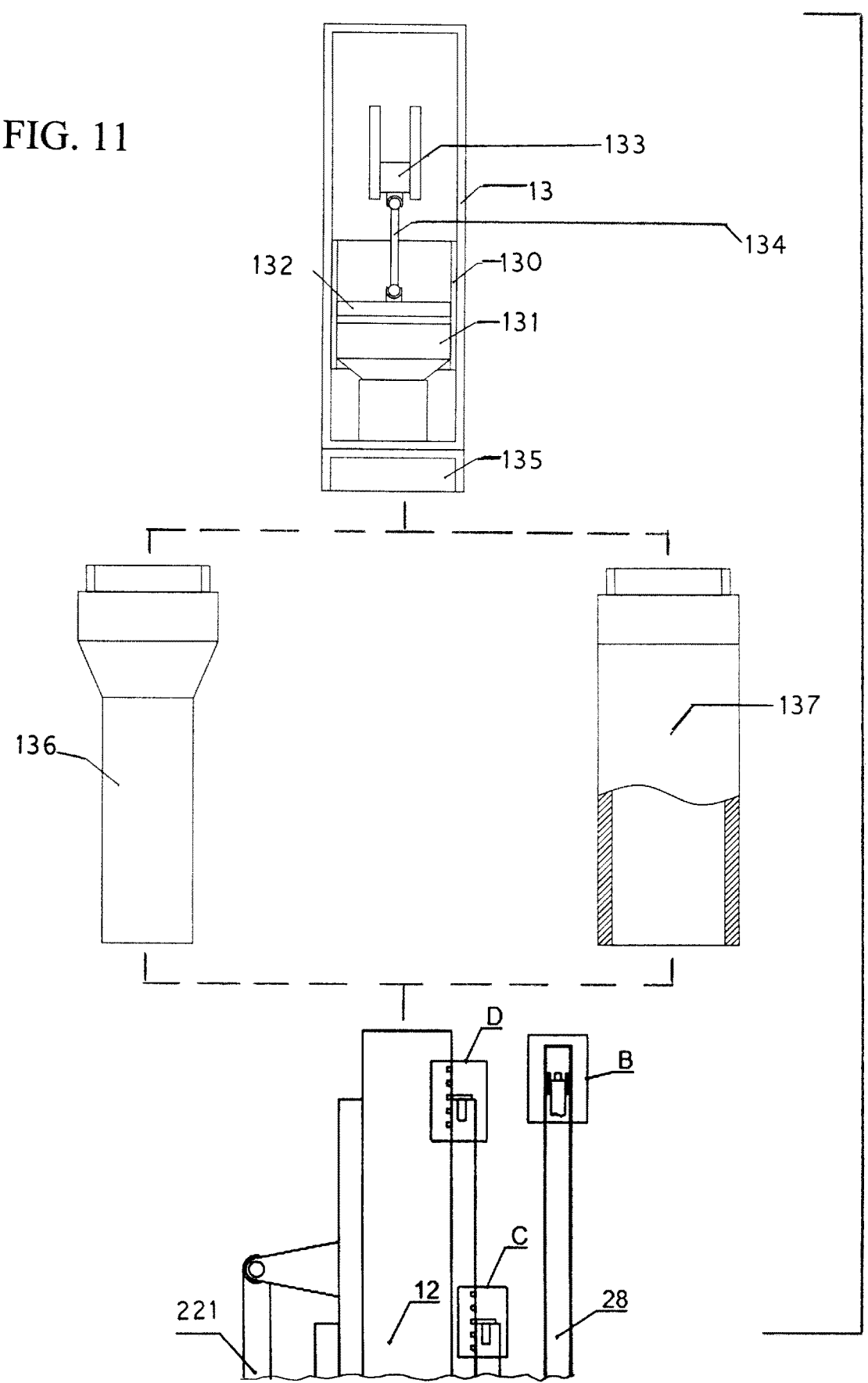
FIG. 11 is an exploded schematic diagram showing the connection of the impact connecting rod of FIG. 9 and the impact connecting cylinder of FIG. 10 to the impact rod of FIG. 8.

As shown in FIG. 9 and FIG. 10, the impact rod 13 is matched with an impact connecting rod 136 and an impact connecting cylinder 137. A lower end of the impact rod 13 is provided with a threaded connecting pipe 135. Upper ends of the impact connecting rod 136 and the impact connecting cylinder 137 can be matched and fixedly connected with the threaded connecting pipe 135. A lower end of the impact connecting rod 136 can be matched and fixedly connected with the top of the connecting sliding rod 12. An outer diameter of the impact connecting rod 136 needs to be smaller than an inner diameter of the stripping sliding cylinder 21. The impact connecting cylinder 137 is of a cylindrical structure with a downward opening. A lower end of the impact connecting cylinder 137 can be matched and fixedly connected with the top of the stripping sliding cylinder 21. An inner diameter of the impact connecting cylinder 137 needs to be larger than an outer diameter of the connecting sliding rod 12.

As shown in FIG. 1, the auxiliary support frame 30 includes a stable support cylinder 31 connected to the outer side of the stripping sliding cylinder 21 in a sliding fit mode. A stable support plate 32 is fixedly arranged on the stable support cylinder 31. A lower side of the stable support plate 32 is connected with a plurality of telescopic stable legs 33.

An upper end of the stable leg 33 is connected with the lower side of the stable support plate 32 through a living hinge. The stable leg 33 includes a leg fixing cylinder 331 and a leg telescopic rod 332 in sliding fit in the leg fixing cylinder 331. Sliding damping of the leg telescopic rod 332 in the leg fixing cylinder 331 is adjustable. A socket cone 333 is fixedly arranged at a lower end of the leg telescopic rod 332.

Figure 5:
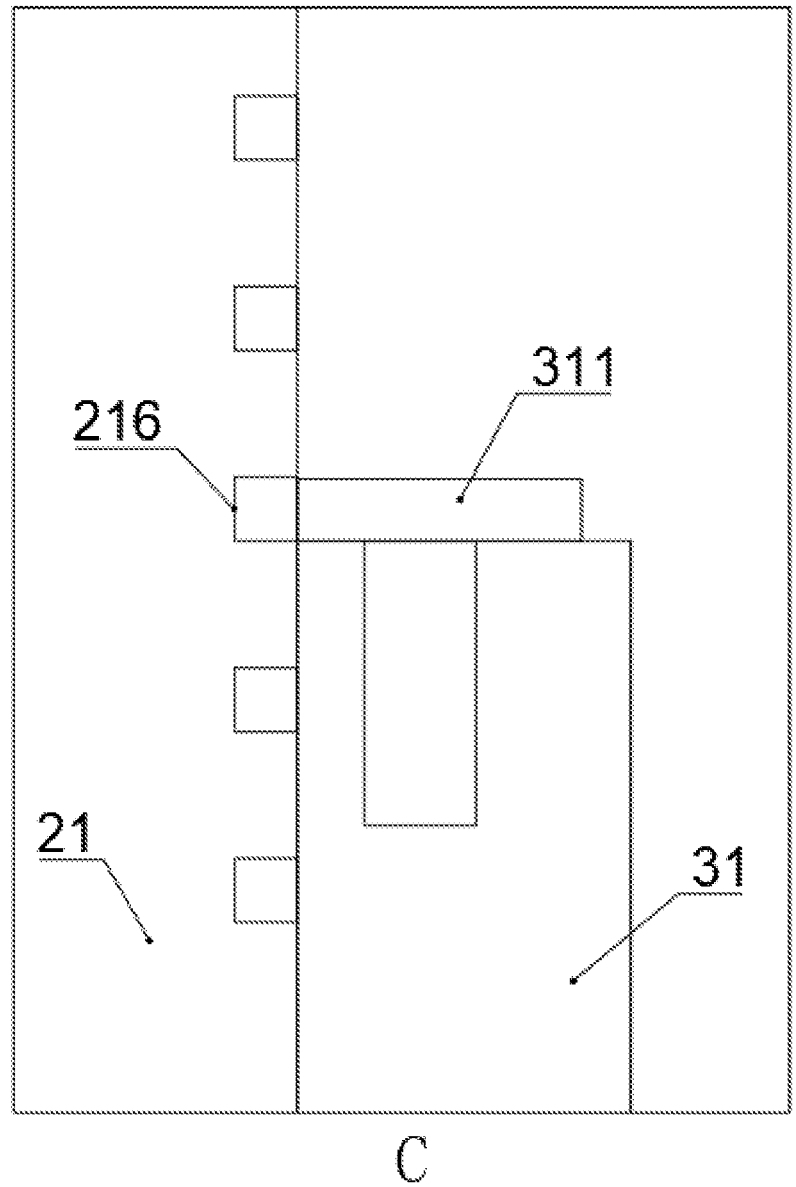
FIG. 5 is a partial view C of FIG. 1.
Figure 6:
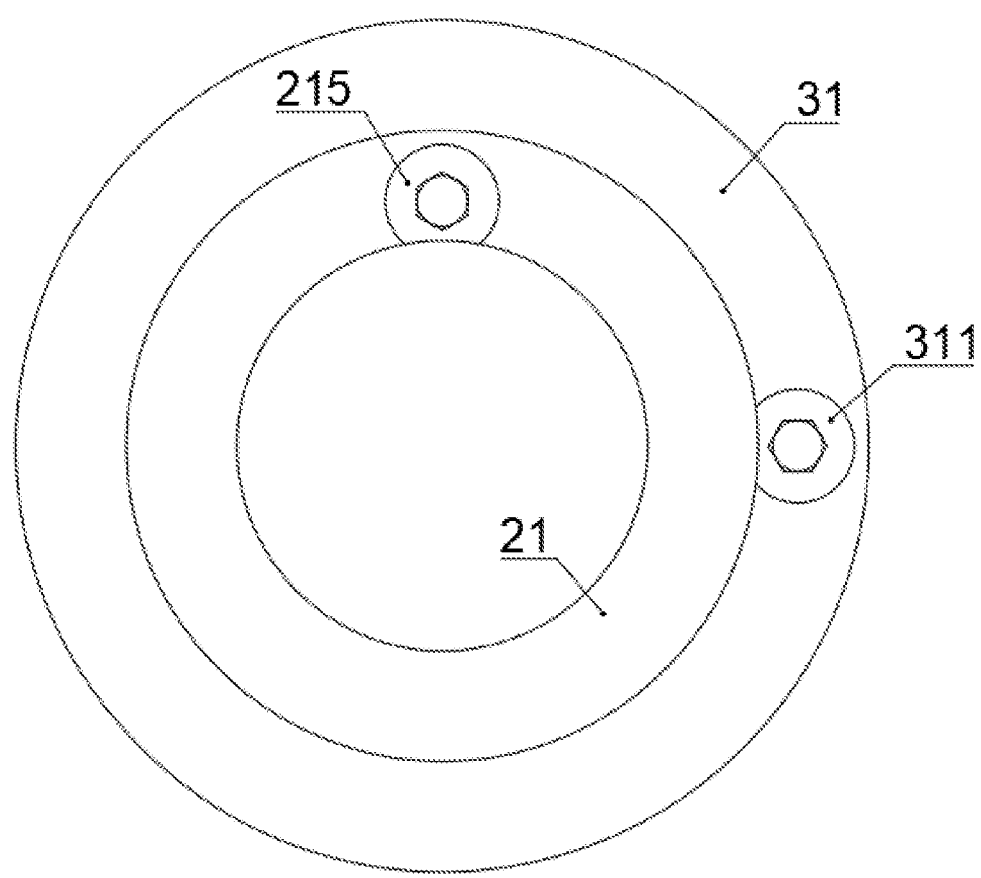
FIG. 6 is a top view of a stable support cylinder in the present disclosure.
Figure 7:
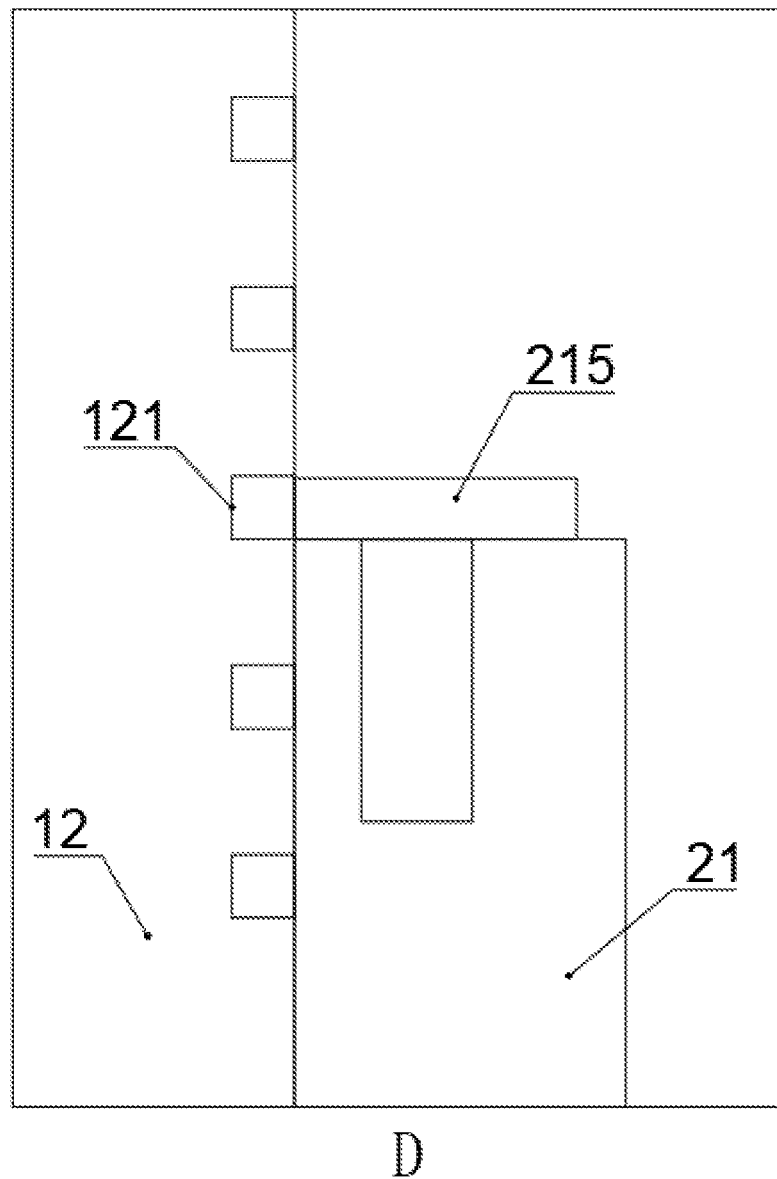
FIG. 7 is a partial view D of FIG. 1.

As shown in FIG. 5, FIG. 6 and FIG. 7, the top of the stable support cylinder 31 is provided with a first limit locking screw 311 in a running fit mode. The top of the stripping sliding cylinder 21 is provided with a second limit locking screw 215 in a running fit mode.

A plurality of first locking grooves 216 are formed in the outer side of the stripping sliding cylinder 21. A plurality of second locking grooves 121 are formed in the outer side of the connecting sliding rod 12.

A screw cap of the first limit locking screw 311 can be clamped in the first locking groove 216. A screw cap of the second limit locking screw 215 can be clamped in the second locking groove 121.

A notch consistent with radian of an outer side wall of the stripping sliding cylinder 21 is formed in the screw cap of the first limit locking screw 311. A notch consistent with radian of an outer side wall of the connecting sliding rod 12 is formed in the screw cap of the second limit locking screw 215.

Embodiment II

Figure 8:
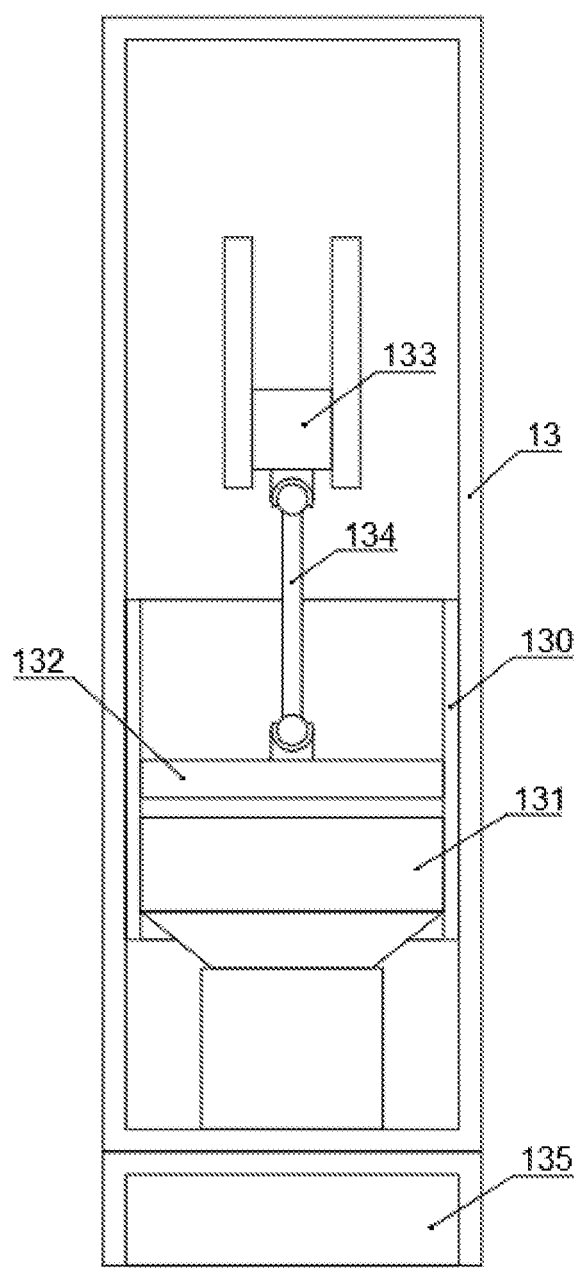
FIG. 8 is a structural schematic diagram of an impact rod in the present disclosure.

As shown in FIG. 8, the difference from the first embodiment lies in that the impact hammer 131 in the impact rod 13 is driven by a linear motor to reciprocate along the axis of the impact rod 13.

A piston cylinder 130 is fixedly arranged in the impact rod 13. The impact hammer 131 is in sliding fit in the piston cylinder 130. A driving piston 132 is arranged in the piston cylinder 130 in a sliding fit mode above the impact hammer 131. A linear motor 133 extending along an axial direction of the impact rod 13 is fixedly arranged in the impact rod 13. An impact driving rod 134 is connected between a rotor of the linear motor 133 and the top of the driving piston 132. Both ends of the impact driving rod 134 are connected in the form of spherical hinges.

Embodiment III

A soil sampling method for a high geological background area by using the sampling device for evaluating ecological risk of soil in a high geological background area includes the following steps:
  S1, firstly, leveling a surface of a position to be sampled, then placing the whole device at the position to be sampled, and inserting the socket cone 333 at the lower end of the leg telescopic rod 332 into the ground to stably support the whole device;
  S2, connecting the impact rod 13 with the top of the connecting sliding rod 12, and inserting the sampling hopper 11 into the soil under the impact effect of a reciprocating motion of the impact hammer 131 in the impact rod 13, so that a soil sample is accommodated in the sampling hopper 11;
  S3, dismantling the impact rod 13 from the top of the connecting sliding rod 12 and then connecting the impact rod 13 with the top of the stripping sliding cylinder 21, and impacting and inserting the stripping plates 22 into the soil under the impact effect of the reciprocating motion of the impact hammer 131 in the impact rod 13, so that the outer side of the sampling hopper 11 is surrounded by the stripping plates 22;

S4, driving the first gear 232 to rotate by a motor, then driving the stripping plate control ring 23 to rotate and driving the lifting drive disc 233 to move downwards along an axis of the stripping plate control ring 23, further driving the wedge block 24 to move by the lifting driving disc 233, and forcing the stripping plate 22 to get away from the sampling hopper 11 in the moving process by the wedge block 24;

S5, after a gap is formed between the stripping plates 22 and the sampling hopper 11, enabling the telescopic rod 281 together with the rotating rod 283 and the cutting plate 284, to move downwards in the gap between the stripping plates 22 and the sampling hopper 11 under the driving of the first motor 285;

S6, when an upper surface of the cutting plate 284 is flush with a lower end face of the sampling hopper 11, driving the rotating rod 283 to rotate by the second motor 286 and driving the cutting plate 284 to cut and strip the soil sample in the sampling hopper 11 from the outside; and S7, finally, separately detaching the sampling hopper 11 together with the connecting sliding rod 12, connecting the impact rod 13 with the top of the connecting sliding rod 12, and separating the soil sample in the sampling hopper 11 by the impact effect of the impact rod 13 and putting the soil sample into a sample container.

Embodiment IV

The difference from the third embodiment lies in that when the whole equipment is in a special situation of power shortage, in steps S2 and S3, the sampling hopper 11 is inserted into the soil by manually hammering the connecting sliding rod 12, and a plurality of stripping plates 22 are impacted and inserted into the soil by manually hammering the stripping sliding cylinder 21. In step S4, the first gear 232 is manually driven to rotate, and then the stripping plate control ring 23 is driven to rotate and the lifting driving disc 233 is driven to move downward along the axis of the stripping plate control ring 23. The lifting driving disc 233 further drives the wedge block 24. The wedge block 24 can force the stripping plate 22 to get away from the sampling hopper 11 in the moving process.

The invention claimed is:

1. A sampling device for evaluating ecological risk of soil in a high geological background area, comprising an impact sampling mechanism (10), a soil layer stripping mechanism (20) and an auxiliary support frame (30), wherein
   the impact sampling mechanism (10) comprises a sampling hopper (11) with a downward opening, a connecting sliding rod (12) is fixedly arranged on the top of the sampling hopper (11), and an upper end of the connecting sliding rod (12) is connected with a hollow impact rod (13);
   the impact rod (13) is internally provided with an impact hammer (131) which is motor-driven to reciprocate within the impact rod (13) along an axis of the impact rod (13) through a crank-link mechanism;
   the soil layer stripping mechanism (20) comprises a stripping sliding cylinder (21) in sliding fit with the connecting sliding rod (12), a support disc (211) is fixedly arranged on the stripping sliding cylinder (21), a plurality of stripping plates (22) are connected to a lower side edge of the support disc (211) in a sliding fit mode, and the stripping plates (22) are motor-driven and can move along a radial direction of the support disc (211);
   the stripping plates (22) are combined into an annular structure surrounding an outer side of the sampling hopper (11), and dimensions of the annular structure combined by the stripping plates (22) along an axial direction of the sampling hopper (11) are larger than axial dimensions of the sampling hopper (11);
   the auxiliary support frame (30) comprises a stable support cylinder (31) connected to the outer side of the stripping sliding cylinder (21) in a sliding fit mode, a stable support plate (32) is fixedly arranged on the stable support cylinder (31), and a lower side of the stable support plate (32) is connected with a plurality of telescopic stable legs (33);
   a plurality of sector ring accommodating grooves (213) are formed in a lower side of the support disc (211), and a plurality of telescopic through holes (214) running from top to bottom are formed in the support disc (211) and located at the sector ring accommodating grooves (213);
   a telescopic control column (28) is fixedly arranged on the top of the support disc (211) at one of the telescopic through holes (214), the telescopic control column (28) is of a hollow structure, the telescopic control column (28) is internally provided with a telescopic rod (281) in a sliding fit mode, a rotating fit hole (282) running from top to bottom is formed in the telescopic rod (281), and the rotating fit hole (282) is internally provided with a rotating rod (283) in a running fit mode;
   a low end of the rotating rod (283) extends through one of the telescopic through holes (214), and a cutting plate (284) is fixedly arranged at a lower end of the rotating rod (283);
   a first motor (285) is fixedly arranged in the top of the telescopic control column (28), the first motor (285) drives the telescopic rod (281) to move along an axis of the telescopic control column (28) through a screw lead mechanism, a second motor (286) is fixedly arranged on the top of the telescopic rod (281), and the second motor (286) is used for driving the rotating rod (283) to rotate in the rotating fit hole (282); and
   a driving fit plate (287) is fixedly arranged on the telescopic rod (281), a threaded hole (288) running from top to bottom is formed in the driving fit plate (287), a threaded rod (289) is fixedly arranged on an output shaft of the first motor (285), and the threaded rod (289) is in threaded running fit in the threaded hole (288).

2. The sampling device for evaluating ecological risk of soil in a high geological background area according to claim 1, wherein the impact hammer (131) in the impact rod (13) is driven by a linear motor (133) to reciprocate along the axis of the impact rod (13); and
   a piston cylinder (130) is fixedly arranged in the impact rod (13), the impact hammer (131) is in sliding fit in the piston cylinder (130), a driving piston (132) is arranged in the piston cylinder (130) in a sliding fit mode above the impact hammer (131), the linear motor (133) extending along an axial direction of the impact rod (13) is fixedly arranged in the impact rod (13), an impact driving rod (134) is connected between a rotor of the linear motor (133) and the top of the driving piston (132), and both ends of the impact driving rod (134) are connected in the form of spherical hinges.

3. The sampling device for evaluating ecological risk of soil in a high geological background area according to claim 1, wherein a plurality of radial sliding grooves (212) extending along the radial direction and running from top to down are formed in the support disc (211), a stripping plate connecting rod (221) is fixedly arranged on the top of one of the stripping plates (22), the stripping plate connecting rod (221) extends upward through one of the radial sliding grooves (212), and an upper end of the stripping plate connecting rod (221) is connected with the stripping sliding cylinder (21) in the form of a living hinge;

a reset spring (222) is arranged between an inner side wall, away from the stripping sliding cylinder (21), of one of the radial sliding grooves (212) and one side, away from the stripping sliding cylinder (21), of the stripping plate connecting rod (221) in a jacking fit mode, and one side, close to the stripping sliding cylinder (21), of the stripping plate connecting rod (221) is provided with a wedge block (24) in a sliding fit mode;

the outer side of the stripping sliding cylinder (21) is connected with a stripping plate control ring (23) in a screw thread fit mode, a first gear ring (231) is fixedly arranged on the stripping plate control ring (23), the outer side of the stripping sliding cylinder (21) is connected with a first gear (232) in a running fit mode, the first gear (232) is connected with the first gear ring (231) in a meshed mode, and the first gear (232) is motor-driven; and a lifting driving disc (233) is fixedly at a lower end of the stripping plate control ring (23), a lifting constraint slot (241) is formed in one side, close to the stripping sliding cylinder (21), of the wedge block (24), and an edge of the lifting driving disc (233) is constrained in the lifting constraint slot (241).

4. The sampling device for evaluating ecological risk of soil in a high geological background area according to claim 3, wherein a manual driving cylinder (234) is fixedly arranged on the top of the first gear (232), and an inner hexagonal hole is formed in the top of the manual driving cylinder (234).

5. The sampling device for evaluating ecological risk of soil in a high geological background area according to claim 4, wherein upper and lower ends of the lifting constraint slot (241) are provided with end face constraint rollers (242) in a running fit mode, and an inner side wall, close to the stripping sliding cylinder (21), of one of the radial sliding grooves (212) is connected with a lateral constraint roller (243) in a running fit mode.

6. The sampling device for evaluating ecological risk of soil in a high geological background area according to claim 1, wherein an upper end of each of the stable legs (33) is connected with the lower side of the stable support plate (32) through a living hinge, each of the stable legs (33) comprises a leg fixing cylinder (331) and a leg telescopic rod (332) in sliding fit in the leg fixing cylinder (331), and sliding damping of the leg telescopic rod (332) in the leg fixing cylinder (331) is adjustable; and a socket cone (333) is fixedly arranged at a lower end of the leg telescopic rod (332).

7. The sampling device for evaluating ecological risk of soil in a high geological background area according to claim 1, wherein the top of the stable support cylinder (31) is provided with a first limit locking screw (311) in a running fit mode, and the top of the stripping sliding cylinder (21) is provided with a second limit locking screw (215) in a running fit mode;

a plurality of first locking grooves (216) are formed in the outer side of the stripping sliding cylinder (21), and a plurality of second locking grooves (121) are formed in the outer side of the connecting sliding rod (12);

a screw cap of the first limit locking screw (311) can be clamped in the first locking grooves (216), and a screw cap of the second limit locking screw (215) can be clamped in the second locking grooves (121); and a notch consistent with radian of an outer side wall of the stripping sliding cylinder (21) is formed in the screw cap of the first limit locking screw (311), and a notch consistent with radian of an outer side wall of the connecting sliding rod (12) is formed in the screw cap of the second limit locking screw (215).

8. The sampling device for evaluating ecological risk of soil in a high geological background area according to claim 1, wherein the impact rod (13) is matched with an impact connecting rod (136) and an impact connecting cylinder (137), a lower end of the impact rod (13) is provided with a threaded connecting pipe (135), upper ends of the impact connecting rod (136) and the impact connecting cylinder (137) can be matched and fixedly connected with the threaded connecting pipe (135), a lower end of the impact connecting rod (136) can be matched and fixedly connected with the top of the connecting sliding rod (12), an outer diameter of the impact connecting rod (136) is smaller than an inner diameter of the stripping sliding cylinder (21), the impact connecting cylinder (137) is of a cylindrical structure with a downward opening, a lower end of the impact connecting cylinder (137) can be matched and fixedly connected with the top of the stripping sliding cylinder (21), and an inner diameter of the impact connecting cylinder (137) is larger than an outer diameter of the connecting sliding rod (12).

9. The sampling device for evaluating ecological risk of soil in a high geological background area according to claim 1, wherein:

a plurality of radial sliding grooves (212) extending along the radial direction and running from top to down are formed in the support disc (211), a stripping plate connecting rod (221) is fixedly arranged on the top of one of the stripping plates (22), the stripping plate connecting rod (221) extends upward through one of the radial sliding grooves (212), and an upper end of the stripping plate connecting rod (221) is connected with the stripping sliding cylinder (21) in the form of a living hinge;

a reset spring (222) is arranged between an inner side wall, away from the stripping sliding cylinder (21), of one of the radial sliding grooves (212) and one side, away from the stripping sliding cylinder (21), of the stripping plate connecting rod (221) in a jacking fit mode, and one side, close to the stripping sliding cylinder (21), of the stripping plate connecting rod (221) is provided with a wedge block (24) in a sliding fit mode;

the outer side of the stripping sliding cylinder (21) is connected with a stripping plate control ring (23) in a screw thread fit mode, a first gear ring (231) is fixedly arranged on the stripping plate control ring (23), the outer side of the stripping sliding cylinder (21) is connected with a first gear (232) in a running fit mode, the first gear (232) is connected with the first gear ring (231) in a meshed mode, and the first gear (232) is motor-driven;

a lifting driving disc (233) is fixedly at a lower end of the stripping plate control ring (23), a lifting constraint slot (241) is formed in one side, close to the stripping sliding cylinder (21), of the wedge block (24), and an edge of the lifting driving disc (233) is constrained in the lifting constraint slot (241); and an upper end of each of the stable legs (33) is connected with the lower side of the stable support plate (32) through a living hinge, each of the stable legs (33) comprises a leg fixing cylinder (331) and a leg telescopic rod (332) in sliding fit in the leg fixing cylinder (331), and sliding damping of the leg telescopic rod (332) in the leg fixing cylinder (331) is adjustable; and a socket cone (333) is fixedly arranged at a lower end of the leg telescopic rod (332).

10. A soil sampling method for a high geological background area by using the sampling device for evaluating ecological risk of soil in a high geological background area according to claim 9, comprising the following steps:

S1, firstly, leveling a surface of a position to be sampled, then placing the whole sampling device according to claim 9 at the position to be sampled, and inserting the socket cone (333) at the lower end of each leg telescopic rod (332) into the ground to stably support the whole device;

S2, connecting the impact rod (13) with the top of the connecting sliding rod (12), and inserting the sampling hopper (11) into the soil under the impact effect of a reciprocating motion of the impact hammer (131) in the impact rod (13), so that a soil sample is accommodated in the sampling hopper (11);

S3, dismantling the impact rod (13) from the top of the connecting sliding rod (12) and then connecting the impact rod (13) with the top of the stripping sliding cylinder (21), and impacting and inserting the stripping plates (22) into the soil under the impact effect of the reciprocating motion of the impact hammer (131) in the impact rod (13), so that the outer side of the sampling hopper (11) is surrounded by the stripping plates (22);

S4, driving the first gear (232) to rotate by a motor or manually, then driving the stripping plate control ring (23) to rotate and driving the lifting drive disc (233) to move downwards along an axis of the stripping plate control ring (23), further driving the wedge block (24) to move by the lifting driving disc (233), and forcing the stripping plates (22) to get away from the sampling hopper (11) in the moving process by the wedge block (24);

S5, after a gap is formed between the stripping plates (22) and the sampling hopper (11), enabling the telescopic rod (281), together with the rotating rod (283) and the cutting plate (284), to move downwards in the gap between the stripping plates (22) and the sampling hopper (11) under the driving of the first motor (285);

S6, when an upper surface of the cutting plate (284) is flush with a lower end face of the sampling hopper (11), driving the rotating rod (283) to rotate by the second motor (286) and driving the cutting plate (284) to cut and strip the soil sample in the sampling hopper (11) from the outside; and S7, finally, separately detaching the sampling hopper (11) together with the connecting sliding rod (12), connecting the impact rod (13) with the top of the connecting sliding rod (12), and separating the soil sample in the sampling hopper (11) by the impact effect of the impact rod (13) and putting the soil sample into a sample container.

11. The sampling device for evaluating ecological risk of soil in a high geological background area according to claim 9, wherein the impact hammer (131) in the impact rod (13) is driven by a linear motor (133) to reciprocate along the axis of the impact rod (13); and a piston cylinder (130) is fixedly arranged in the impact rod (13), the impact hammer (131) is in sliding fit in the piston cylinder (130), a driving piston (132) is arranged in the piston cylinder (130) in a sliding fit mode above the impact hammer (131), the linear motor (133) extending along an axial direction of the impact rod (13) is fixedly arranged in the impact rod (13), an impact driving rod (134) is connected between a rotor of the linear motor (133) and the top of the driving piston (132), and both ends of the impact driving rod (134) are connected in the form of spherical hinges.

12. A soil sampling method for a high geological background area by using the sampling device for evaluating ecological risk of soil in a high geological background area according to claim 11, comprising the following steps:

S1, firstly, leveling a surface of a position to be sampled, then placing the whole sampling device according to claim 11 at the position to be sampled, and inserting the socket cone (333) at the lower end of each leg telescopic rod (332) into the ground to stably support the whole device;

S2, connecting the impact rod (13) with the top of the connecting sliding rod (12), and inserting the sampling hopper (11) into the soil under the impact effect of a reciprocating motion of the impact hammer (131) in the impact rod (13), so that a soil sample is accommodated in the sampling hopper (11);

S3, dismantling the impact rod (13) from the top of the connecting sliding rod (12) and then connecting the impact rod (13) with the top of the stripping sliding cylinder (21), and impacting and inserting the stripping plates (22) into the soil under the impact effect of the reciprocating motion of the impact hammer (131) in the impact rod (13), so that the outer side of the sampling hopper (11) is surrounded by the stripping plates (22);

S4, driving the first gear (232) to rotate by a motor or manually, then driving the stripping plate control ring (23) to rotate and driving the lifting drive disc (233) to move downwards along an axis of the stripping plate control ring (23), further driving the wedge block (24) to move by the lifting driving disc (233), and forcing the stripping plates (22) to get away from the sampling hopper (11) in the moving process by the wedge block (24);

S5, after a gap is formed between the stripping plates (22) and the sampling hopper (11), enabling the telescopic rod (281), together with the rotating rod (283) and the cutting plate (284), to move downwards in the gap between the stripping plates (22) and the sampling hopper (11) under the driving of the first motor (285);

S6, when an upper surface of the cutting plate (284) is flush with a lower end face of the sampling hopper (11), driving the rotating rod (283) to rotate by the second motor (286) and driving the cutting plate (284) to cut and strip the soil sample in the sampling hopper (11) from the outside; and S7, finally, separately detaching the sampling hopper (11) together with the connecting sliding rod (12), connecting the impact rod (13) with the top of the connecting sliding rod (12), and separating the soil sample in the sampling hopper (11) by the impact effect of the impact rod (13) and putting the soil sample into a sample container.

13. The sampling device for evaluating ecological risk of soil in a high geological background area according to claim 9, wherein a manual driving cylinder (234) is fixedly arranged on the top of the first gear (232), and an inner hexagonal hole is formed in the top of the manual driving cylinder (234).

14. A soil sampling method for a high geological background area by using the sampling device for evaluating ecological risk of soil in a high geological background area according to claim 13, comprising the following steps:
S1, firstly, leveling a surface of a position to be sampled, then placing the whole sampling device according to claim 13 at the position to be sampled, and inserting the socket cone (333) at the lower end of each leg telescopic rod (332) into the ground to stably support the whole device;
S2, connecting the impact rod (13) with the top of the connecting sliding rod (12), and inserting the sampling hopper (11) into the soil under the impact effect of a reciprocating motion of the impact hammer (131) in the impact rod (13), so that a soil sample is accommodated in the sampling hopper (11);
S3, dismantling the impact rod (13) from the top of the connecting sliding rod (12) and then connecting the impact rod (13) with the top of the stripping sliding cylinder (21), and impacting and inserting the stripping plates (22) into the soil under the impact effect of the reciprocating motion of the impact hammer (131) in the impact rod (13), so that the outer side of the sampling hopper (11) is surrounded by the stripping plates (22);
S4, driving the first gear (232) to rotate by a motor or manually, then driving the stripping plate control ring (23) to rotate and driving the lifting drive disc (233) to move downwards along an axis of the stripping plate control ring (23), further driving the wedge block (24) to move by the lifting driving disc (233), and forcing the stripping plates (22) to get away from the sampling hopper (11) in the moving process by the wedge block (24);
S5, after a gap is formed between the stripping plates (22) and the sampling hopper (11), enabling the telescopic rod (281), together with the rotating rod (283) and the cutting plate (284), to move downwards in the gap between the stripping plates (22) and the sampling hopper (11) under the driving of the first motor (285);
S6, when an upper surface of the cutting plate (284) is flush with a lower end face of the sampling hopper (11), driving the rotating rod (283) to rotate by the second motor (286) and driving the cutting plate (284) to cut and strip the soil sample in the sampling hopper (11) from the outside; and
S7, finally, separately detaching the sampling hopper (11) together with the connecting sliding rod (12), connecting the impact rod (13) with the top of the connecting sliding rod (12), and separating the soil sample in the sampling hopper (11) by the impact effect of the impact rod (13) and putting the soil sample into a sample container.

15. The sampling device for evaluating ecological risk of soil in a high geological background area according to claim 13, wherein upper and lower ends of the lifting constraint slot (241) are provided with end face constraint rollers (242) in a running fit mode, and an inner side wall, close to the stripping sliding cylinder (21), of one of the radial sliding grooves (212) is connected with a lateral constraint roller (243) in a running fit mode.

16. A soil sampling method for a high geological background area by using the sampling device for evaluating ecological risk of soil in a high geological background area according to claim 15, comprising the following steps:
S1, firstly, leveling a surface of a position to be sampled, then placing the whole sampling device according to claim 15 at the position to be sampled, and inserting the socket cone (333) at the lower end of each leg telescopic rod (332) into the ground to stably support the whole device;
S2, connecting the impact rod (13) with the top of the connecting sliding rod (12), and inserting the sampling hopper (11) into the soil under the impact effect of a reciprocating motion of the impact hammer (131) in the impact rod (13), so that a soil sample is accommodated in the sampling hopper (11);
S3, dismantling the impact rod (13) from the top of the connecting sliding rod (12) and then connecting the impact rod (13) with the top of the stripping sliding cylinder (21), and impacting and inserting the stripping plates (22) into the soil under the impact effect of the reciprocating motion of the impact hammer (131) in the impact rod (13), so that the outer side of the sampling hopper (11) is surrounded by the stripping plates (22);
S4, driving the first gear (232) to rotate by a motor or manually, then driving the stripping plate control ring (23) to rotate and driving the lifting drive disc (233) to move downwards along an axis of the stripping plate control ring (23), further driving the wedge block (24) to move by the lifting driving disc (233), and forcing the stripping plates (22) to get away from the sampling hopper (11) in the moving process by the wedge block (24);
S5, after a gap is formed between the stripping plates (22) and the sampling hopper (11), enabling the telescopic rod (281), together with the rotating rod (283) and the cutting plate (284), to move downwards in the gap between the stripping plates (22) and the sampling hopper (11) under the driving of the first motor (285);
S6, when an upper surface of the cutting plate (284) is flush with a lower end face of the sampling hopper (11), driving the rotating rod (283) to rotate by the second motor (286) and driving the cutting plate (284) to cut and strip the soil sample in the sampling hopper (11) from the outside; and
S7, finally, separately detaching the sampling hopper (11) together with the connecting sliding rod (12), connecting the impact rod (13) with the top of the connecting sliding rod (12), and separating the soil sample in the sampling hopper (11) by the impact effect of the impact rod (13) and putting the soil sample into a sample container.

17. The sampling device for evaluating ecological risk of soil in a high geological background area according to claim 9, wherein the top of the stable support cylinder (31) is provided with a first limit locking screw (311) in a running fit mode, and the top of the stripping sliding cylinder (21) is provided with a second limit locking screw (215) in a running fit mode;
a plurality of first locking grooves (216) are formed in the outer side of the stripping sliding cylinder (21), and a plurality of second locking grooves (121) are formed in the outer side of the connecting sliding rod (12);
a screw cap of the first limit locking screw (311) can be clamped in the first locking grooves (216), and a screw cap of the second limit locking screw (215) can be clamped in the second locking grooves (121); and
a notch consistent with radian of an outer side wall of the stripping sliding cylinder (21) is formed in the screw cap of the first limit locking screw (311), and a notch consistent with radian of an outer side wall of the connecting sliding rod (12) is formed in the screw cap of the second limit locking screw (215).

18. A soil sampling method for a high geological background area by using the sampling device for evaluating ecological risk of soil in a high geological background area according to claim 17, comprising the following steps:
- S1, firstly, leveling a surface of a position to be sampled, then placing the whole sampling device according to claim 17 at the position to be sampled, and inserting the socket cone (333) at the lower end of each leg telescopic rod (332) into the ground to stably support the whole device;
- S2, connecting the impact rod (13) with the top of the connecting sliding rod (12), and inserting the sampling hopper (11) into the soil under the impact effect of a reciprocating motion of the impact hammer (131) in the impact rod (13), so that a soil sample is accommodated in the sampling hopper (11);
- S3, dismantling the impact rod (13) from the top of the connecting sliding rod (12) and then connecting the impact rod (13) with the top of the stripping sliding cylinder (21), and impacting and inserting the stripping plates (22) into the soil under the impact effect of the reciprocating motion of the impact hammer (131) in the impact rod (13), so that the outer side of the sampling hopper (11) is surrounded by the stripping plates (22);
- S4, driving the first gear (232) to rotate by a motor or manually, then driving the stripping plate control ring (23) to rotate and driving the lifting drive disc (233) to move downwards along an axis of the stripping plate control ring (23), further driving the wedge block (24) to move by the lifting driving disc (233), and forcing the stripping plates (22) to get away from the sampling hopper (11) in the moving process by the wedge block (24);
- S5, after a gap is formed between the stripping plates (22) and the sampling hopper (11), enabling the telescopic rod (281), together with the rotating rod (283) and the cutting plate (284), to move downwards in the gap between the stripping plates (22) and the sampling hopper (11) under the driving of the first motor (285);
- S6, when an upper surface of the cutting plate (284) is flush with a lower end face of the sampling hopper (11), driving the rotating rod (283) to rotate by the second motor (286) and driving the cutting plate (284) to cut and strip the soil sample in the sampling hopper (11) from the outside; and
- S7, finally, separately detaching the sampling hopper (11) together with the connecting sliding rod (12), connecting the impact rod (13) with the top of the connecting sliding rod (12), and separating the soil sample in the sampling hopper (11) by the impact effect of the impact rod (13) and putting the soil sample into a sample container.

19. The sampling device for evaluating ecological risk of soil in a high geological background area according to claim 9, wherein the impact rod (13) is matched with an impact connecting rod (136) and an impact connecting cylinder (137), a lower end of the impact rod (13) is provided with a threaded connecting pipe (135), upper ends of the impact connecting rod (136) and the impact connecting cylinder (137) can be matched and fixedly connected with the threaded connecting pipe (135), a lower end of the impact connecting rod (136) can be matched and fixedly connected with the top of the connecting sliding rod (12), an outer diameter of the impact connecting rod (136) is smaller than an inner diameter of the stripping sliding cylinder (21), the impact connecting cylinder (137) is of a cylindrical structure with a downward opening, a lower end of the impact connecting cylinder (137) can be matched and fixedly connected with the top of the stripping sliding cylinder (21), and an inner diameter of the impact connecting cylinder (137) is larger than an outer diameter of the connecting sliding rod (12).

20. A soil sampling method for a high geological background area by using the sampling device for evaluating ecological risk of soil in a high geological background area according to claim 19, comprising the following steps:
- S1, firstly, leveling a surface of a position to be sampled, then placing the whole sampling device according to claim 19 at the position to be sampled, and inserting the socket cone (333) at the lower end of each leg telescopic rod (332) into the ground to stably support the whole device;
- S2, connecting the impact rod (13) with the top of the connecting sliding rod (12), and inserting the sampling hopper (11) into the soil under the impact effect of a reciprocating motion of the impact hammer (131) in the impact rod (13), so that a soil sample is accommodated in the sampling hopper (11);
- S3, dismantling the impact rod (13) from the top of the connecting sliding rod (12) and then connecting the impact rod (13) with the top of the stripping sliding cylinder (21), and impacting and inserting the stripping plates (22) into the soil under the impact effect of the reciprocating motion of the impact hammer (131) in the impact rod (13), so that the outer side of the sampling hopper (11) is surrounded by the stripping plates (22);
- S4, driving the first gear (232) to rotate by a motor or manually, then driving the stripping plate control ring (23) to rotate and driving the lifting drive disc (233) to move downwards along an axis of the stripping plate control ring (23), further driving the wedge block (24) to move by the lifting driving disc (233), and forcing the stripping plates (22) to get away from the sampling hopper (11) in the moving process by the wedge block (24);
- S5, after a gap is formed between the stripping plates (22) and the sampling hopper (11), enabling the telescopic rod (281), together with the rotating rod (283) and the cutting plate (284), to move downwards in the gap between the stripping plates (22) and the sampling hopper (11) under the driving of the first motor (285);
- S6, when an upper surface of the cutting plate (284) is flush with a lower end face of the sampling hopper (11), driving the rotating rod (283) to rotate by the second motor (286) and driving the cutting plate (284) to cut and strip the soil sample in the sampling hopper (11) from the outside; and
- S7, finally, separately detaching the sampling hopper (11) together with the connecting sliding rod (12), connecting the impact rod (13) with the top of the connecting sliding rod (12), and separating the soil sample in the sampling hopper (11) by the impact effect of the impact rod (13) and putting the soil sample into a sample container.

\* \* \* \* \*